United States Patent [19]
Devereux et al.

[11] Patent Number: 5,092,884
[45] Date of Patent: Mar. 3, 1992

[54] SURGICAL COMPOSITE STRUCTURE HAVING ABSORBABLE AND NONABSORBABLE COMPONENTS

[75] Inventors: Dennis F. Devereux, Pennington, N.J.; Henry P. Landi, Yorktown Heights, N.Y.

[73] Assignee: American Cyanamid Company, Stamford, Conn.

[21] Appl. No.: 560,452

[22] Filed: Jul. 25, 1990

Related U.S. Application Data

[63] Continuation-in-part of Ser. No. 172,607, Mar. 24, 1988, abandoned.

[51] Int. Cl.$^5$ ................................................ A61F 2/02
[52] U.S. Cl. .................................................... 623/11
[58] Field of Search ........................... 623/1, 11, 16; 128/335.5

[56] References Cited

U.S. PATENT DOCUMENTS

| | | | |
|---|---|---|---|
| 3,992,725 | 11/1976 | Homsy | 623/16 |
| 4,052,988 | 10/1977 | Doddi et al. | 128/335.5 |
| 4,137,921 | 2/1979 | Okuzumi | 623/1 |
| 4,201,216 | 5/1980 | Mattei | 128/335.5 |
| 4,205,399 | 6/1980 | Shalaby et al. | 128/335.5 |
| 4,226,243 | 10/1980 | Shalaby et al. | 128/335.5 |
| 4,340,091 | 7/1982 | Skelton et al. | 623/1 |
| 4,429,080 | 1/1984 | Casey et al. | 525/415 |
| 4,461,298 | 7/1984 | Shalaby et al. | 128/335.5 |
| 4,576,608 | 3/1986 | Homsy | 623/11 |
| 4,610,688 | 9/1986 | Silvestrini et al. | 623/1 |
| 4,643,734 | 2/1987 | Lin | 623/16 |
| 4,652,264 | 3/1987 | Dumican | 623/11 |
| 4,661,530 | 4/1987 | Gogolewski et al. | 623/16 |
| 4,719,917 | 1/1988 | Barrows et al. | 128/335.5 |
| 4,754,758 | 7/1988 | Li | 128/334 C |
| 4,759,765 | 7/1988 | Van Kampen | 623/13 |
| 4,791,929 | 12/1988 | Jarrett et al. | 128/335.5 |
| 4,792,336 | 12/1988 | Hlavacek et al. | 623/13 |
| 4,834,755 | 5/1989 | Silvestrini et al. | 623/13 |

FOREIGN PATENT DOCUMENTS

| | | |
|---|---|---|
| 0194192 | 9/1986 | European Pat. Off. . |
| 2577807 | 8/1986 | France . |
| 1008193 | 10/1965 | United Kingdom . |
| 86533 | 1/1986 | World Int. Prop. O. . |

*Primary Examiner*—John D. Yasko
*Assistant Examiner*—Sharon Finkel
*Attorney, Agent, or Firm*—Charles F. Costello, Jr.

[57] ABSTRACT

A composite structure is disclosed having two or more biocompatible polymers. At least one of the polymers is nonabsorbable. The nonabsorbable polymer is extruded into a fiber. The fiber can be fabricated into a textile structure, for example a woven mesh. The nonabsorbable mesh is then encapsulated with at least one bioabsorbable polymer. The composite structure is useful for repairing anatomical defects, for example in a mammalian abdominal wall.

4 Claims, No Drawings

SURGICAL COMPOSITE STRUCTURE HAVING ABSORBABLE AND NONABSORBABLE COMPONENTS

This application is a continuation-in-part of application Ser. No. 07/172,607 filed Mar. 24, 1988 now abandoned.

BACKGROUND OF THE INVENTION

This invention relates to a surgical composite structure. The structure is manufactured from two or more biocompatible polymers. At least one of the polymers in the structure is nonabsorbable.

The nonabsorbable polymer is extruded into a fiber. The fiber can be fabricated into a textile structure. The textile structure can be a woven mesh. The nonabsorbable woven mesh is then encapsulated with at least one bioabsorbable polymer.

The nonabsorbable portion of the composite structure acts as a reinforcement material. Ingrowth of natural tissue is enhanced by the controlled degradation of the absorbable portion.

The surgical composite structure of this invention is useful in the repair of defects to the abdominal wall of a mammal. The surgical composite structure of this invention may be useful in preventing hernia formation; and specifically in preventing hernia formation in an infected area.

SUMMARY AND DESCRIPTION OF THE PREFERRED EMBODIMENT(S)

A surgical composite structure for mammalian tissue has been invented. The composite structure comprises:
a) a nonabsorbable reinforcing component prepared from one or more fibers, at least one of the fibers manufactured from a polymer selected from the group consisting of a fiber forming fluoropolymer, polybutester, polyester, polyamide, polyolefin, and blends of the same, and
b) a bioabsorbable component comprising a polymer prepared from one or more monomers selected from the group consisting of lactides, carbonates, oxalates and lactones.

In one embodiment, the nonabsorbable component is selected from the group consisting of a fiber forming fluoropolymer, a polybutester, and a polyester.

In another embodiment, the bioabsorbable component comprises a polymer prepared from one or more monomers selected from the group consisting of lactides, carbonates and lactones. In a specific embodiment the lactides are selected from the group consisting of glycolide and 3,6-dimethyl-2,5-p-dioxanedione; the carbonate is 1,3-dioxan-2-one; and the lactones are $\epsilon$-caprolactone and 1,4-dioxan-2-one. In another specific embodiment, the bioabsorbable component is selected from the group consisting of lactides and carbonates.

In yet another embodiment, the nonabsorbable component is in the form of a sheet. In a specific embodiment, the bioabsorbable component is laminated to at least one side of the sheet. In a more specific embodiment, the bioabsorbable component is laminated to both sides of the sheet. In another specific embodiment, the nonabsorbable component is in the form of a knitted, woven, flat braided, or nonwoven sheet. In a preferred embodiment, the nonabsorbable component is in the form of a woven sheet.

An alternative surgical composite structure for mammalian tissue has been invented. The alternative structure comprises:
a) a nonabsorbable reinforcing component prepared from a plurality of fibers, at least one of the fibers manufactured from a polymer selected from the group consisting of a fiber forming fluoropolymer, a polybutester, a polyester, and blends of the same, and
b) a bioabsorable component comprising a polymer prepared from one or more monomers selected from the group consisting of lactides, carbonates and lactones.

In one embodiment the lactides are selected from the group consisting of glycolide and 3,6-dimethyl-2,5-p-dioxanedione; the carbonate is 1,3-dioxan-2-one; and the lactones are selected from the group consisting of $\epsilon$-caprolactone and 1,4-dioxan-2-one.

In a specific embodiment, the bioabsorbable component is manufactured from the monomers glycolide and 1,3-dioxan-2-one. In another specific embodiment, the nonabsorbable component is in the form of a knitted or woven sheet.

Another alternative surgical composite structure for mammalian tissue has been invented. The structure comprises:
a) a nonabsorable woven component prepared from a plurality of fibers, the fibers comprising a polymer selected from the group consisting of polytetrafluoroethylene, a copolymer of tetrafluoroethylene and hexafluoropropylene, perfluoroalkoxy resin, ethylene-chlorotrifluoroethylene copolymer, ethylene-tertafluoroethylene copolymer, and polyvinylidene fluoride, and
b) a bioabsorbable component laminated to the nonabsorbable woven component, the bioabsorbable component comprising a polymer prepared from at least two monomers selected from the group consisting of lactides, carbonates and lactones.

In one embodiment, the nonabsorbable woven component is selected from the group consisting of polytetrafluoroethylene, a copolymer of tetrafluoroethylene and hexafluoropropylene, and polyvinylidene fluoride. In a specific embodiment, the nonabsorbable woven component consists of a copolymer of tetrafluoroethylene and hexafluoropropylene.

In another specific embodiment, the bioabsorbable component comprises a random copolymer. In a more specific embodiment, the random copolymer is prepared from at least the monomers glycolide and 1,3-dioxan-2-one.

Yet another alternative surgical composite structure for mammalian tissue has been invented. The structure comprises:
a) a nonabsorbable woven component prepared from a plurality of fibers, the fibers comprising a polymer selected from the group consisting of a polybutester and polybutylene terephthalate, and
b) a bioabsorbable component laminated to the nonabsorbable woven component, the bioabsorbable component comprising a polymer prepared from at least two monomers selected from the group consisting of lactides, carbonates and lactones.

In a specific embodiment, the nonabsorbable woven component is a polybutester.

In another specific embodiment, the bioabsorbable component comprises a random copolymer. In a more specific embodiment, the random copolymer is prepared from at least the monomers glycolide and 1,3-dioxan-2-one.

A drawing which describes the shape and/or geometrical configuration of the surgical composite structure is not necessary for an understanding of this invention. That is, any person skilled in the surgical composite structure art will know how to manufacture and how to use the invention by reading this specification, generally and the examples, specifically.

It is to be understood that the bioabsorbable component can be coated onto the nonabsorbable reinforcing component by any coating means known in the prior art. The inventors have found that lamination is an adequate means for coating. Specifically, the inventors have found that bonding the bioabsorbable component to the nonabsorbable reinforcing component by fusion is an adequate means of laminating the two components. However, other forms of coating, such as encapsulation, are within the scope of this invention.

Throughout this disclosure, it is to be understood that the term Teflon is a trademark of the E. I. DuPont and Company, DE, U.S.A., whether the term Teflon is or is not so identified as a trademark.

The term fluoropolymer is generic and includes the terms fluoroplastic and fluoroelastomer. For a disclosure of fluoroplastics, see Modern Plastics Encyclopedia vol. 64 no. 10A (1987) pages 31–32, McGraw-Hill, N.Y., which is incorporated herein by reference. The Teflon TM FEP described in the examples is a copolymer of tetrafluoroethylene and hexafluoropropylene. It is also to be understood that the term polybutester as used in this disclosure is synonymous with the terms polyetherester, polyether-ester or polyether ester. A commercially available polybutester is the Hytrel TM (E. I. DuPont and Co.) copolymer.

Preferred embodiments of this invention are more fully described in the Examples 1 to 6, below.

COMPARATIVE EXAMPLE A

A woven mesh, identified as Style T-151-56 and supplied by Stern & Stern Textiles, Inc., Hugnet Fabrics Div., Hornell, N.Y. 14843, is used as a control for the composite meshes of Examples 1 and 2, below. It is made with monofilament fibers of Teflon TM FEP polymer with a diameter of 5 to 6 mils (or 0.005 inch to 0.006 inch). These fibers are woven into a mesh configuration of approximately 80×90 strands per inch. The overall thickness of the woven fabric is approximately 12 mils (or 0.012 inch).

EXAMPLE 1

A composite structure consisting of a fabric of a woven mesh made up of biocompatible, nonabsorbable, monofilament fibers is encapsulated by lamination between two films of a bioabsorbable polymer.

Specifically, the woven mesh is identified as Style T-151-56 and is supplied by Stern & Stern Textiles, Inc., Hugnet Fabrics Div., Hornell, N.Y. 14843. It is made with monofilament fibers of Teflon FEP polymer with a diameter of 5 to 6 mils (or 0.005 inch to 0.006 inch). These fibers are woven into a mesh configuration of approximately 80×90 strands per inch. The overall thickness of the woven fabric is approximately 12 mils (or 0.012 inch).

The films of bioabsorbable polymer used in the laminated composite are prepared by compression molding a random copolymer of 50/50 weight percent of glycolide trimethylene carbonate to a thickness of approximately 10 mils (or 0.010 inch) thick. The manufacture of the random copolymer is described, without the need for undue experimentation, in the prior art. See, e.g., the preparation of random copolymers described in U.S. Pat. No. 3,736,646, which issued June 5, 1973 and U.S. Pat. No. 3,867,190 entitled "Reducing Capillarity of Polyglycolic Acid Sutures", which issued Feb. 18, 1975, both patents being issued to E. Schmitt and M. Epstein and incorporated herein by reference.

The conditions for molding these films is as follows. A pre-dried, preformed pellet of approximately 5.0 grams of the copolymer is placed between two 7 inch×7 inch caul plates and Teflon PTFE release film. This assembly is placed in a 6 inch×6 inch Carver Laboratory Press which is pre-heated to 145° C.±5° C. and gradually increased in pressure to 1,000 lbs. force on a 1¾ inch diameter ram. The pressure is held constant for 3 minutes. Subsequently, this assembly is removed from the press and cooled to approximately 15° C. while still under press. The film is then easily released from between the Teflon release film. The resultant film is a transparent, amber-colored film of approximately mils (0.010 inch) thick ×5 inches×5 inches.

The final composite structure is formed by laminating a film of the copolymer on either side of the Teflon FEP woven mesh between two 7 inch×7 inch caul plates and Teflon PTFE release film. This assembly is placed in a 6 inch×6 inch Carver Laboratory Press which is pre-heated to 145° C.±5° C. and gradually increased in pressure to 1,000 lbs. force. The pressure is held constant for approximately 3 minutes. Subsequently, this assembly is removed from the press and cooled to approximately 15° C. while still under pressure. The laminated composite structure is then easily released from between the Teflon PTFE release film. The resultant laminated composite consists of a Teflon FEP woven fabric which is completely encapsulated within the fused copolymer of 50/50 weight percent poly-(glycolide-co-trimethylene carbonate). The resultant laminated composite is approximately 20 mils (0.020 inch) thick and 5 inches×5 inches in size.

EXAMPLE 2

A composite laminated structure is prepared similar to that described in Example 1 except the polymer films are made with a random copolymer of 68/32 weight percent of glycolide trimethylene carbonate substituted for the 50/50 weight percent copolymer. The preparation of the random copolymer is described, without the need for undue experimentation, in the prior art. See, e.g., the preparation of random copolymers described in U. S. Pat. No. 3,736,646, which issued June 5, 1973 and U.S. Pat. No. 3,867,190 entitled "Reducing Capillarity of Polyglycolic Acid Sutures", which issued Feb. 18, 1975, both patents being issued to E. Schmitt and M. Epstein and incorporated herein by reference. Also, the processing temperature was increased to approximately 150° C.±5°·C.

EXAMPLE 3

A composite laminated structure is prepared similar to that described in Example 2 except that the woven mesh is made from monofilament fibers of HYTREL ® with a diameter of 5 to 6 mils (0.005 inch to 0.006 inch).

Hytrel ™ (E. I. DuPont and Co.) is a polyether-ester, and can be a polymer of polytetramethylene glycol with terephthalic acid and 1,4-butanediol. These fibers are woven into a mesh configuration of approximately 80×90 strands per inch. The overall thickness of the woven fabric is approximately 12 mils (0.012 inch).

EXAMPLE 4

Sterile, composite structure samples of the type described in Example 1 were implanted in 3 rats to determine the initial efficacy of this composite structure.

At 6 weeks following implantation the composite structure seemed to be associated with much inflammation. At 6 months this did not appear to be the case, and the Teflon FEP mesh component of the composite structure was well-encased in the animal subcutaneous tissues.

EXAMPLE 5

Sterile, composite structure samples of the type described in Comparative Example A and Example 1 were implanted in 36 rats. Each wound area was infected by the introduction of staphylococcus aureus, $E.\ coli$, and bacteriodes in a mixture of $10^5$ organisms per milliliter.

Thirty-two of the 36 rats implanted with the uncoated Teflon FEP woven mesh of Comparative Example A showed clinical signs of infection. All of these results were confirmed histologically. Many white cells were found around the abscess cavity. These were cultured positive for mixtures of organisms which were implanted during the operative placement of the Comparative Example A uncoated Teflon FEP woven mesh.

After 6 months implantation the results indicated that 35 out of the 36 rats were free of infection with implants of the composite structure of Example 1.

EXAMPLE 6

An additional in vivo study was conducted to confirm the advantages of a tissue reinforcing woven mesh made from fibers of a nonabsorbable polymer encapsulated or coated with an absorbable polymer, versus an uncoated mesh, in an infected wound area.

Both sterile, composite structure samples of the type described in Example 2 and uncoated Teflon FEP woven mesh samples described in Comparative Example A were implanted in 18 rabbits. Each animal was implanted with two (2) samples of coated mesh and two (2) samples of uncoated mesh diagonally on shoulder-/hip quadrants. Each wound area was infected as described in Example 5, above.

The results of this study indicated that there was no infection in the areas of the composite structure samples at the end of 6 weeks. In the uncoated Teflon FEP woven mesh wounds all were found to be infected after 6 weeks.

EXAMPLE 7

An in vivo study was conducted in dogs to investigate the effectiveness of a composite structure of the type described in Example 2 in a model more closely resembling the intended commercial use of the material.

Fourteen mongrel dogs were anesthetized and their abdomens were prepared using sterile solutions. Using a midline incision, two-thirds of the left rectus muscle was resected. In eight animals the resected muscle was replaced with uncoated teflong FEP woven mesh (comparative Example A), which was sewn in place using a running polypropylene (PROLENE½) suture. In six animals, coated mesh (Example 2) was used to replace the resected muscle.

All wounds were contaminated with 1 ml of $10^6$ org/ml concentrations of staph aureus and $E.\ Coli$ from human blood isolates. Wounds were closed using stainless steel clips, no antibiotics were given. The temperatures of the animals were recorded daily for two weeks post-operatively. In all cases a sustained elevated temperature was observed, indicating a viable contamination. In each case, some animals were sacrificed at three months for histological examination of the meshes, the remainder being sacrificed after six months of post-operative follow-up. One of the animals with an uncoated mesh implant died of peritonitis prior to the three month interval.

In the three month sacrifice group implantation of the uncoated Teflon mesh resulted in seven out of seven animals manifested draining infected wounds. No exposed mesh was observed, although two small bowel-mesh fistulas were noted. No hernia formation was observed, although the general condition of the animals were considered to be "unhealthy". Three animals were maintained for six months, at which time the condition of the wounds was unchanged, i.e. draining of infected material from the incision site.

In the three month sacrifice group implantation of the coated Teflon mesh resulted in six out of six animals had wound drainage. Four animals demonstrated mesh rejection and exposure (three of these were sacrificed for histological study), and one animal exhibited a small bowel-mesh fistula. After six months one out of the remaining three animals continued to exhibit mesh rejection and exposure.

EXAMPLE 8

A concurrent in vivo study to that described in Example 7 was conducted using identical surgical methods. In this study, six animals were implanted with an uncoated HYTREL ® fiber mesh as described in Example 3. Also, six animals received the coated HYTREL ® fiber mesh described in Example 3. The progress of the animals was followed in the same way as described in Example 7.

After three months implantation of the uncoated HYTREL ® mesh, five out of six animals exhibited draining wounds. After six months, two out of three animals demonstrated wound drainage. No other complications were observed.

After three months implantation of the coated HYTREL ® mesh, none of the animals exhibited wound drainage. After six months one animal of three developed a small amount of drainage due to a piece of the polypropylene suture which had poked through the wound incision. This had occurred after four months implantation. The mesh itself was not exposed and resection of the suture resulted in healing of the site in excess of 2 months. The overall condition of these animals at sacrifice was observed to be good.

Three additional animals were implanted with coated HYTREL ® mesh samples, but were not intentionally contaminated. At three months none of the animals exhibited any complications; at this time one animal was sacrificed for histological examination. No complications were observed at six months for the two remaining animals.

EXAMPLE 9

Three animals from the study in Example 7 that had received coated Teflon FEP mesh implant and that had become chronically infected and had developed rejection and exposure of the mesh at the three month period were used as subjects in an additional clinically relevant study. These animals were treated by resection of the infected mesh, replacement of that infected mesh was with the coated HYTREL ® mesh used in Example 8, and three doses of strep/pen antibiotics were administered. After three months two of the animals wounds had healed. The third animal had died of an intraoperative anesthetic death.

EXAMPLE 10

Four puppies with spontaneously occurring (congenital) umbilical hernias were used for an in vivo evaluation of the coated HYTREL ® mesh (from Examples 3 and 8) for hernia repair, and its effects during growth into an adult dog.

The puppies abdomens were prepped in a sterile manner while under anesthesia and a midline incision was made over the hernia. Entry into the hernia was not complicated by enterotomy although the muscle and falciform ligament was resected in each animal along with the sack for adequate exposure. No antibiotics or contaminants were administered. Coated HYTREL ® mesh was used to replace the resected hernias in all four animals in order to achieve abdominal wall closure.

All four animals grew to normal adulthood (1 year old). No evidence of complications (i.e. obstruction, infection, fistula or impairment of the animal activity) was observed over the course of the study.

What is claimed:

1. A surgical composite structure for mammalian tissue comprising:
    a) a nonabsorable woven component prepared from a plurality of fibers, the fibers comprising a polybutester, and
    b) a film consisting essentially of bioabsorbable component laminated to the nonabsorbable woven component, the bioabsorbable component comprising a random compolymer prepared from at least two monomers selected from the group consisting of lactides, carbonates and lactones.

2. The composite structure of claim 1 wherein the random copolymer is prepared from at least the monomers glycolide and 1,3-dioxan-2-one.

3. A surgical composite structure for mammalian tissue comprising:
    a) a nonabsorbable reinforcing component prepared from a plurality of fibers, at least one of the fibers manufactured from a polymer selected from the group consisting of a polybutester and blends of the same, and
    b) a film consisting essentially of a bioabsorbable component comprising a polymer prepared from the monomers glycolide and 1,3-dioxan-2-one.

4. The composite structure of claim 3 wherein the film of component b) is a laminate.

* * * * *